United States Patent
Lerdahl et al.

(10) Patent No.: US 10,098,772 B2
(45) Date of Patent: Oct. 16, 2018

(54) KINK RESISTANT STENT GRAFT

(75) Inventors: Robert G. Lerdahl, Phoenix, AZ (US); Chandrashekhar Prabhakar Pathak, Phoenix, AZ (US); R. Michael Casanova, Scottsdale, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1933 days.

(21) Appl. No.: 11/869,941

(22) Filed: Oct. 10, 2007

(65) Prior Publication Data

US 2009/0099642 A1    Apr. 16, 2009

(51) Int. Cl.
| A61F 2/06 | (2013.01) |
| A61F 2/966 | (2013.01) |
| A61F 2/07 | (2013.01) |
| A61F 2/915 | (2013.01) |

(52) U.S. Cl.
CPC ............... *A61F 2/966* (2013.01); *A61F 2/07* (2013.01); *A61F 2/915* (2013.01); *A61F 2002/072* (2013.01); *A61F 2240/001* (2013.01)

(58) Field of Classification Search
CPC ............................. A61F 2002/072; A61F 2/07
USPC ....................................................... 623/1.13
See application file for complete search history.

(56) References Cited

U.S. PATENT DOCUMENTS

| 5,725,547 | A | 3/1998 | Chuter |
| 5,928,279 | A | 7/1999 | Shannon et al. |
| 6,053,938 | A | 4/2000 | Goldmann et al. |
| 6,361,637 | B2 | 3/2002 | Martin et al. |
| 6,652,577 | B2 * | 11/2003 | Gianotti ........................ 623/1.22 |
| 7,150,758 | B2 | 12/2006 | Kari et al. |
| 7,244,271 | B2 * | 7/2007 | Lentz et al. ................. 623/1.44 |
| 2004/0049264 | A1 | 3/2004 | Sowinski et al. |
| 2004/0176836 | A1 * | 9/2004 | Kari et al. ................... 623/1.32 |
| 2006/0047336 | A1 * | 3/2006 | Gale et al. ................... 623/1.11 |
| 2009/0030499 | A1 * | 1/2009 | Bebb et al. ................. 623/1.13 |

FOREIGN PATENT DOCUMENTS

| WO | 1998038947 A1 | 9/1998 |
| WO | 2007056762 A2 | 5/2007 |

OTHER PUBLICATIONS

International Search Report and Written Opinion for related matter: PCT/US2008/079610, expected to be published as WO2008/049229A3.
Apr. 22, 2010 International Preliminary Report on Patentability and Written Opinion from International Application No. PCT/US2008/079610 filed Oct. 10, 2008.
Jul. 30, 2009 International Search Report from International Application No. PCT/US2008/079610 filed Oct. 10, 2008.
EP 08837480.6 filed Oct. 10, 2008 Search Report dated Sep. 30, 2010.

\* cited by examiner

*Primary Examiner* — Gregory Anderson
(74) *Attorney, Agent, or Firm* — Rutan & Tucker, LLP

(57) ABSTRACT

A stent graft is disclosed and can include a stent and a graft engaged with the stent. The graft can include an inner surface and an outer surface. Further, at least one of the inner surface and the outer surface can include a plurality of protrusions as viewed in cross section extending through a longitudinal axis.

1 Claim, 15 Drawing Sheets

KINK RESISTANT STENT GRAFT

FIELD OF THE DISCLOSURE

The present disclosure relates generally to surgical devices. More specifically, the present disclosure relates to grafts and stent grafts.

BACKGROUND

A human vascular system includes a heart and numerous veins and arteries connected to the heart. The veins and arteries deliver blood to and from the heart. Injuries can occur in which a vein or an artery is damaged. A damaged artery or a damaged vein can be repaired, or replaced, using a tubular member such as a graft or stent graft. The tubular member can be deployed within the damaged artery or vein to span the damage portion. Alternatively, the damaged portion of the artery or vein can be removed and the tubular member can be sutured in place of the removed portion.

Despite continued improvements in stent graft designs, improved grafts and improved stent grafts are desired. Particularly, stents and stent grafts that have the capability of a wide range of deployment locations and which have robust designs.

DETAILED DESCRIPTION OF THE DRAWINGS

In general, a stent graft is disclosed and can include a stent and a graft engaged with the stent. The graft can include an inner surface and an outer surface. Further, at least one of the inner surface and the outer surface can include a plurality of protrusions as viewed in cross section extending through a longitudinal axis.

In another embodiment, a stent graft is disclosed and can include an inner graft layer and a stent can circumscribe the inner graft layer. Further, an outer graft layer can circumscribe the stent. At least one corrugation can be formed in the inner graft layer and the outer graft layer.

In yet another embodiment, a stent graft is disclosed and can include an inner graft layer and at least one bead can be wound around the inner graft layer. Also, a stent can circumscribe the at least one bead and an outer stent graft layer can circumscribe the stent.

In still another embodiment, a stent graft is disclosed and can include an inner graft layer and a stent can circumscribe the inner graft layer. An outer graft layer can circumscribe the stent and at least one bead can be wound around the outer graft layer.

In another embodiment, a method of making a stent graft is disclosed and can include installing an inner tube on a mandrel and installing a stent over the inner tube. Further, the method can include installing an outer tube over the stent and sintering the outer tube to the inner tube.

In yet still another embodiment, a method of making a stent graft is disclosed and can include installing a tube on a mandrel and installing a coated stent over the tube. Moreover, the method can include sintering the inner tube to the coated stent.

In another embodiment, a method of making a stent graft is disclosed and can include installing an inner tube on a mandrel and winding at least one bead around the inner tube. The method can also include installing a stent over the at least one bead and installing an outer tube over the stent. Additionally, the method can include sintering the outer tube to the inner tube.

In still another embodiment, a method of making a stent graft is disclosed and can include installing an inner tube on a mandrel and installing a stent over the inner tube. Also, the method can include installing an outer tube over the stent and winding at least one bead around the outer tube. Further, the method can include sintering the outer tube to the inner tube and the bead to the outer tube.

Description of a Stent Delivery Device

Figure 1:
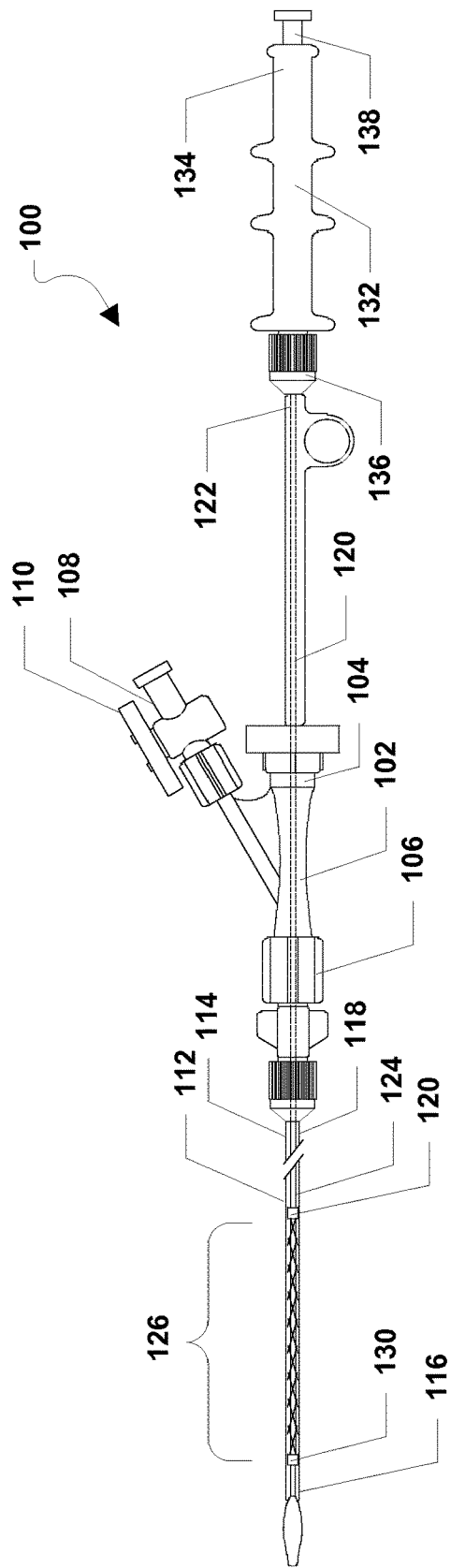
FIG. 1 is a plan view of a corrugated stent graft delivery device.

Referring to FIG. 1, a stent delivery device is shown and is generally designated 100. As shown, the stent delivery device 100 includes a body 102 having a proximal end 104 and a distal end 106. A first syringe attachment 108 can be formed in the body 102 between the proximal end 104 and the distal end 106. In a particular embodiment, the first syringe attachment 108 can be a Luer syringe attachment. The first syringe attachment 108 can provide fluid communication to a lumen formed within an outer sheath 112, described below. Further, the first syringe attachment 108 can include a stopcock 110.

FIG. 1 indicates that the stent delivery device 100 can include an outer sheath 112. The outer sheath 112 can include a proximal end 114 and a distal end 116. Further, the outer sheath 112 can extend from the distal end 106 of the body 102 of the stent delivery device 100. In particular, the proximal end 114 of the outer sheath 112 can be attached to the distal end 106 of the body 102 of the stent delivery device 100. The distal end 116 of the outer sheath 112 can be relatively soft and rounded. The outer sheath 112 can include a lumen 118 formed therein.

As illustrated in FIG. 1, the stent delivery device 100 can further include an inner carrier catheter 120. The inner carrier catheter 120 can extend through the body 102 of the stent delivery device 100 and into the lumen 118 formed in the outer sheath 112. The inner carrier catheter 120 can be coaxial with the outer sheath 112. Further, the inner carrier catheter 120 can include a proximal end 122 and a distal end 124. The inner carrier catheter 120 can be formed with a lumen (not shown) that can be sized to fit over a guide wire. In particular, the lumen of the inner carrier catheter 120 can fit over a 0.035 inch guide wire.

As shown in FIG. 1, a corrugated stent graft 126 can be compressed between the inner catheter 120, e.g., the distal end of the inner catheter 120, and the outer sheath 112. The corrugated stent graft 126 can include a first radiopaque band 128 and a second radiopaque band 130. With the aid of fluoroscopy, the radiopaque bands 128, 130 can facilitate positioning of the corrugated stent graft 126 within a patient.

A handle 132 can be attached to, or otherwise extend from, the proximal end 122 of the inner carrier catheter 120. The handle 132 can include a proximal end 134 and a distal end 136. The proximal end 134 of the handle 132 can include a second syringe attachment 138. In a particular embodiment, the second syringe attachment 138 can be a Luer syringe attachment. The second syringe attachment 138 can provide fluid communication with the lumen formed within the inner carrier catheter 120.

The stent delivery device 100 can also include a safety clip 140 installed between the body 102 of the stent delivery device 100 and the handle 128 of the inner carrier catheter 120. The safety clip 140 can include a proximal end 142 and a distal end 144. Further, the safety clip 140 can include a ring handle 146 between the proximal end 142 of the safety clip 140 and the distal end 144 of the safety clip 140. In a particular embodiment, the safety clip 140 can be installed between the body 102 of the stent delivery device 100 and the handle 128 of the inner carrier catheter 120 such that the proximal end 142 of the safety clip 140 abuts the distal end 132 of the handle 128 and the distal end 144 of the safety clip 140 abuts the proximal end 104 of the body 102.

The safety clip 140 can fit over the inner carrier catheter 120. Further, the safety clip 140 can prevent the body 102 of the stent delivery device 100 from moving relative to the handle 128 of the inner carrier catheter 120. Further, the safety clip 140 can prevent the outer sheath 112 from sliding relative to the inner carrier catheter 120.

As shown in FIG. 1, the stent delivery device 100 can also include a valve 150 engaged with, or installed on, the proximal end 104 of the body 102 of the stent delivery device 100. In a particular embodiment, the valve 150 can be a Tuohy-Borst valve. When the valve 150 is tightened, e.g., by turning the valve 150 clockwise, the inner carrier catheter 120 cannot be moved relative to the outer sheath 112. However, when the valve 150 is loosened, e.g., by turning the valve 150 counterclockwise, the inner carrier catheter 120 can be moved relative to the outer sheath 112.

During use, the stent delivery device 100 can be threaded into a cardiovascular system of a patient to a target area. The radiopaque bands 128, 130 on the corrugated stent graft 126 can be used to guide the stent delivery device into the cardiovascular system of a patient, e.g., with the aid of fluoroscopy. The safety clip 140 can be removed from the inner carrier catheter 120 and the stent delivery device 100 and the valve 150 can be loosened. Thereafter, the body 102 of the stent delivery device 100 can be moved toward the handle of the inner carrier catheter 120 in order to slide the outer sheath 112 off of the corrugated stent graft 126 and expose the corrugated stent graft 126 inside the patient.

Once the corrugated stent graft 126 is exposed within the patient, the corrugated stent graft 126 can automatically deploy due to the body heat of the patient. Further, the corrugated stent graft 126 can move to an expanded shape memory configuration.

Description of a Corrugated Stent Graft

Figure 2:
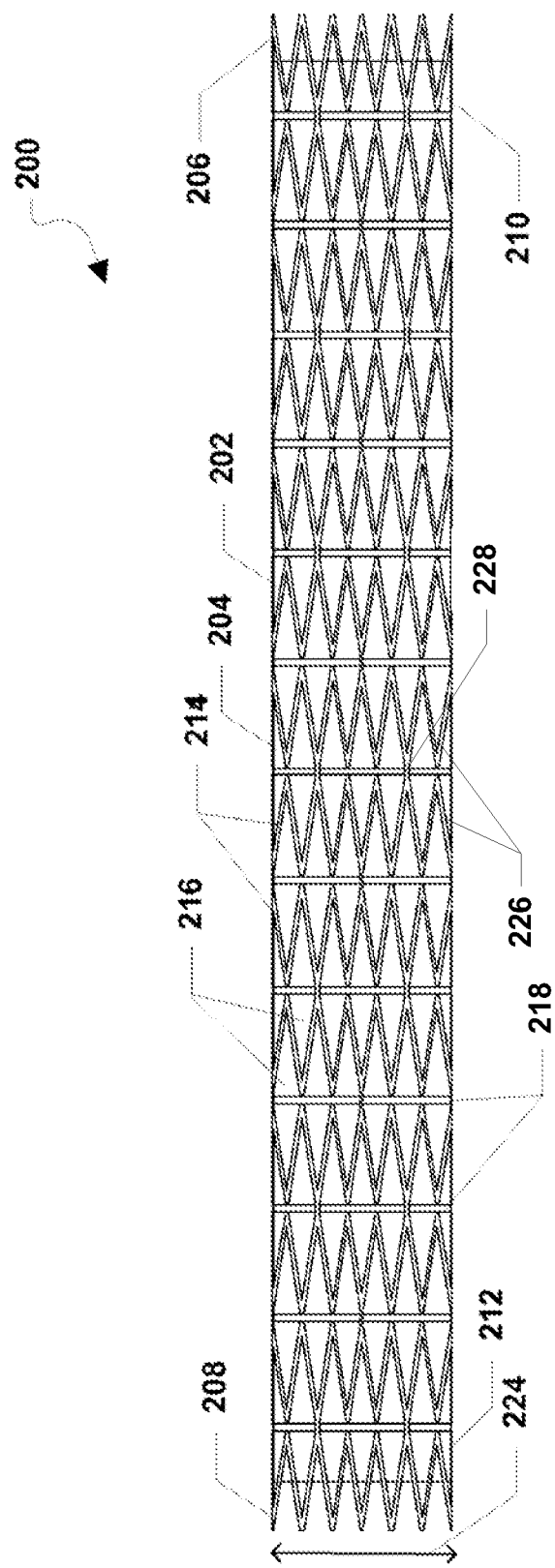
FIG. 2 is a plan view of an embodiment of a corrugated stent graft in a collapsed configuration.
Figure 3:
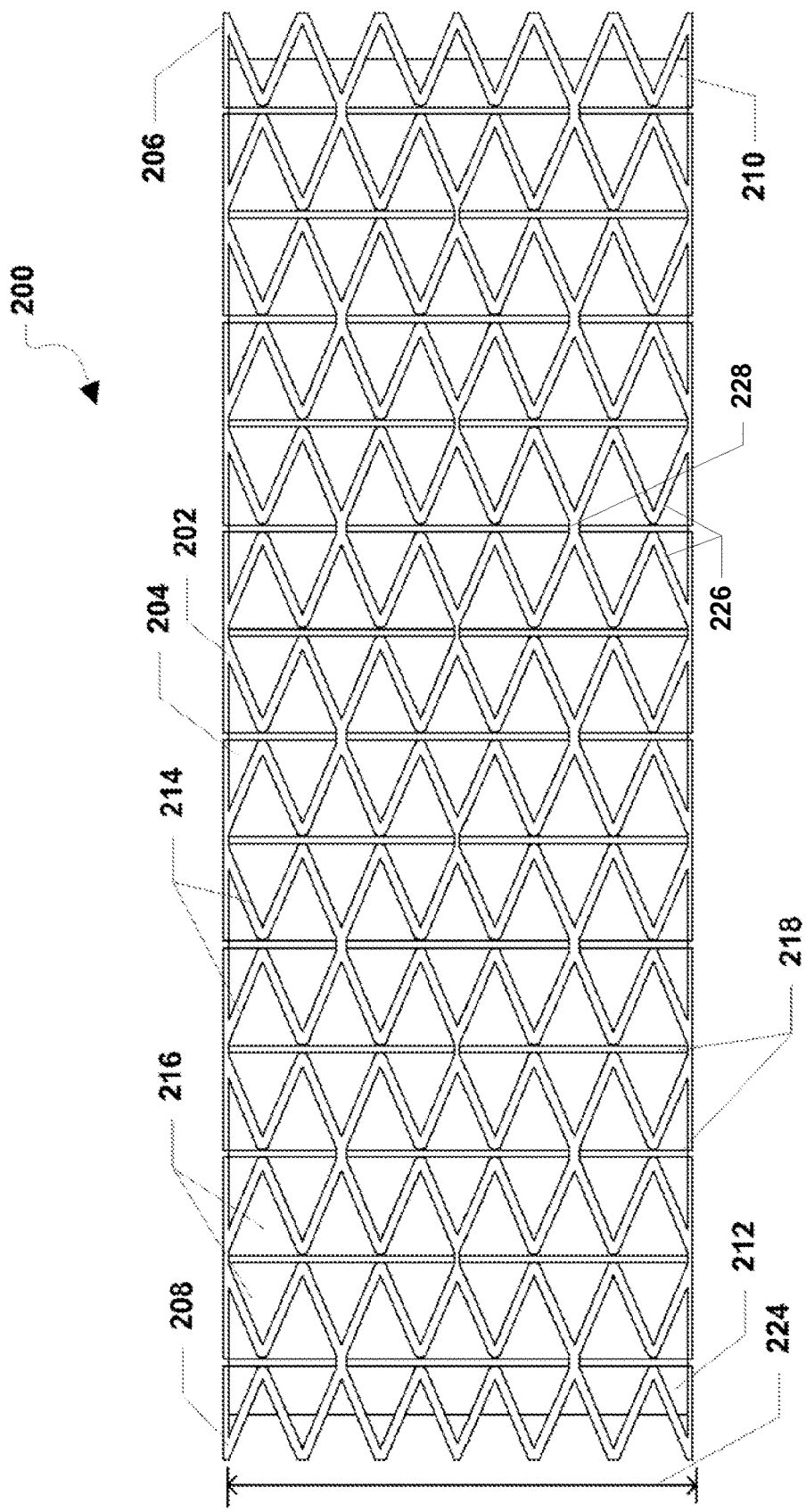
FIG. 3 is a plan view of the corrugated stent graft in an expanded configuration.

Referring to FIG. 2 and FIG. 3, a corrugated stent graft is shown and is generally designated 200. As shown, the corrugated stent graft 200 can include a stent 202 and a graft 204. The stent 202 can be hollow and generally cylindrical. Further, the stent 202 can include a proximal end 206 and a distal end 208. The graft 204 can also be hollow and generally cylindrical. Also, the graft 204 can include a proximal end 210 and a distal end 212.

As indicated in FIG. 2 and FIG. 3, the stent 202 can include a plurality of struts 214. Further, the struts 214 can be arranged to form a plurality of rings 226 that establish a plurality of cells 216 within the stent 202. As shown, the struts 214 are arranged in a generally zig-zag formation to form individual rings 226. The struts of adjacent rings 226 may be directly connected. For example, a connecting strut 228 may join adjacent rings 226 by connecting a point of one ring to a point of an adjacent ring. The point of connection between rings may be at the vertex of two struts within a ring. One or more connecting struts may be used to connect adjacent rings. FIG. 2 and FIG. 3 also show that the graft 204 can include a plurality of protrusions, e.g., a plurality of corrugations 218, when viewed in cross section through a longitudinal axis of the stent graft 200. In a particular embodiment, the corrugations 218 can be generally annular. Further, each corrugation can form a closed loop. Alternatively, the corrugations 218 can be generally helically shaped. In a particular embodiment, the corrugations 218 can improve the flexibility of the corrugated stent graft 200 and substantially minimize the likelihood of the corrugated stent graft 200 kinking when it is bent, e.g., after the corrugated stent graft 200 is installed.

As shown in FIG. 2 and FIG. 3, the corrugations 218 can be formed in the graft 206 so that each corrugation 218 is perpendicular to a longitudinal axis of the stent graft 200. Further, each corrugation 218 can bisect a plurality of cells 216 extending radially around the stent 202. In another embodiment, the corrugations 218 can be angled with respect to a longitudinal axis and the cells 216 can be oriented at an angle with respect to the longitudinal axis, so that each cell 216 is bisected by a corrugation 218.

In a particular embodiment, the shape of the stent 202 can promote, or facilitate, bending of the stent 202 within the cells 216, e.g., through groups of cells 216 around the stent 202. The arrangement of each corrugation 218 through a group of cells 216, places each corrugation 218 in such locations along the stent graft 200 to facilitate bending of the stent graft 200 while substantially preventing the stent graft 200 from kinking.

Further, due to the shape, or configuration, of the stent 202, each of the corrugations 218 formed in the graft 206 may not be continuous around the stent 202. For example, the graft 206 can be corrugated within a series of adjacent cells 218, but the corrugation may be discontinuous over one or more struts 214 that establish the cells 218.

In a particular embodiment, the corrugated stent graft 200 can include a predetermined number of corrugations per inch (in) length of the corrugated stent graft 200. For example, the corrugated stent graft 200 can include at least forty corrugations per inch (40/in). In another embodiment, the corrugated stent graft 200 can include at least fifty corrugations per inch (50/in). In yet another embodiment, the corrugated stent graft 200 can include at least sixty corrugations per inch (60/in). In another embodiment, the corrugated stent graft 200 can include at least seventy corrugations per inch (70/in). In another embodiment, the corrugated stent graft 200 can include at least eighty corrugations per inch (80/in). In another embodiment, the corrugated stent graft 200 can include at least ninety corrugations per inch (90/in). In another embodiment, the corrugated stent graft 200 can include at least one hundred corrugations per inch (100/in). In another embodiment, the corrugated stent graft 200 can include at least one hundred and twenty corrugations per inch (120/in). In another embodiment, the corrugated stent graft 200 can include no more than one hundred and fifty corrugations per inch (150/in).

Figure 4:
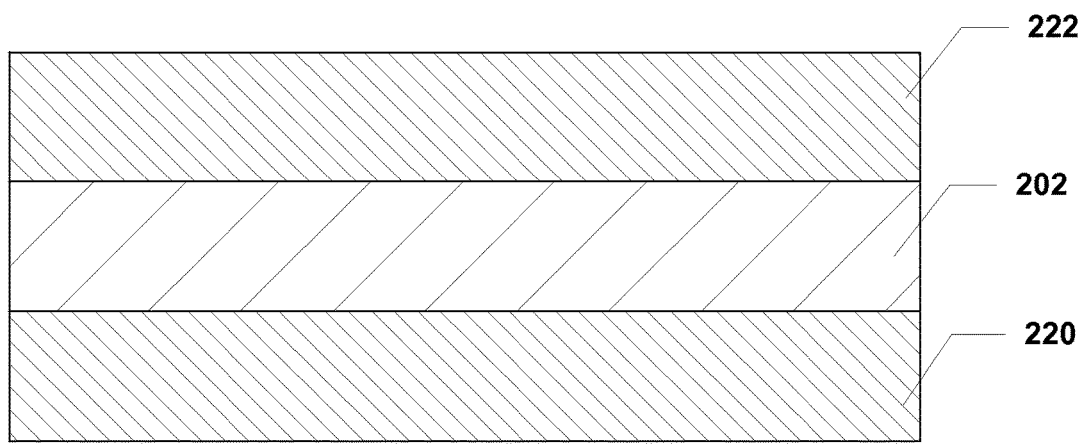
FIG. 4 is a cross-section view of a portion of the first corrugated stent graft.

As shown in FIG. 4, which is a cross-section of the corrugated stent graft at a strut, the stent 202 can be sandwiched, or otherwise formed, between a first graft layer 220 and a second graft layer 222. In another embodiment, the stent 202 can be formed around a single graft layer. In yet another embodiment, the stent 202 can be formed within a single graft layer. In each embodiment, the stent 202 and graft 204 can form an integral structure and as the stent 202 expands, as described below, the graft 204 can expand therewith. Further, as the stent 202 is bent, the graft 204 can bend therewith.

In a particular embodiment the corrugated stent graft 200 can be formed without the stent 202. In such a case, the corrugated stent graft 200 can be considered a corrugated graft. Further, such a corrugated graft can be formed using one of the methods described herein.

In another particular embodiment, the corrugated stent graft 200 can be movable between a collapsed configuration, shown in FIG. 2, and an expanded configuration, shown in FIG. 3. FIG. 2 and FIG. 3 show that the corrugated stent graft 200 can have a diameter 224. The diameter 224 of the corrugated stent graft 200, in the collapsed configuration, is relatively smaller than the diameter 224 of the corrugated stent graft 200 in the expanded configuration. In the collapsed configuration, the cells 216 within the stent 202 can be collapsed, or otherwise compressed, as indicated in FIG. 2. Conversely, in the expanded configuration the cells 216 within the stent body 202 can be expanded, as indicated in FIG. 3.

Further, the corrugated stent graft 200 can have a relatively low kink radius. In other words, the corrugated stent graft 200 can be bent around a particular radius without kinking. For example, the corrugated stent graft 200 can have a kink radius less than or equal to twenty millimeters (20 mm). In another embodiment, the corrugated stent graft 200 can have a kink radius less than or equal to fifteen millimeters (15 mm). In another embodiment, the corrugated stent graft 200 can have a kink radius less than or equal to ten millimeters (10 mm). In another embodiment, the corrugated stent graft 200 can have a kink radius less than or equal to five millimeters (5 mm). In another embodiment, the corrugated stent graft 200 can have a kink radius that is not less than three millimeters (3 mm).

In a particular embodiment, the stent 202 of the corrugated stent graft 200 can be made from a shape memory material. The shape memory material can include a shape memory polymer, a shape memory metal, or a combination thereof. Further, the shape memory metal can include a metal alloy. The metal alloy can be a nickel titanium alloy, e.g., nitinol. Further, the graft 204 of the corrugated stent graft 200 can be made from a polymer material. In a particular embodiment, the polymer material can be a fluoropolymer material. Moreover, the fluoropolymer material can be an expanded polytetrafluoroethylene (ePTFE). In a particular embodiment, the corrugated stent graft 200 can be formed using one of the methods described in conjunction with FIG. 4 through FIG. 7.

Description of a Method of Making a Corrugated Graft

Figure 5:
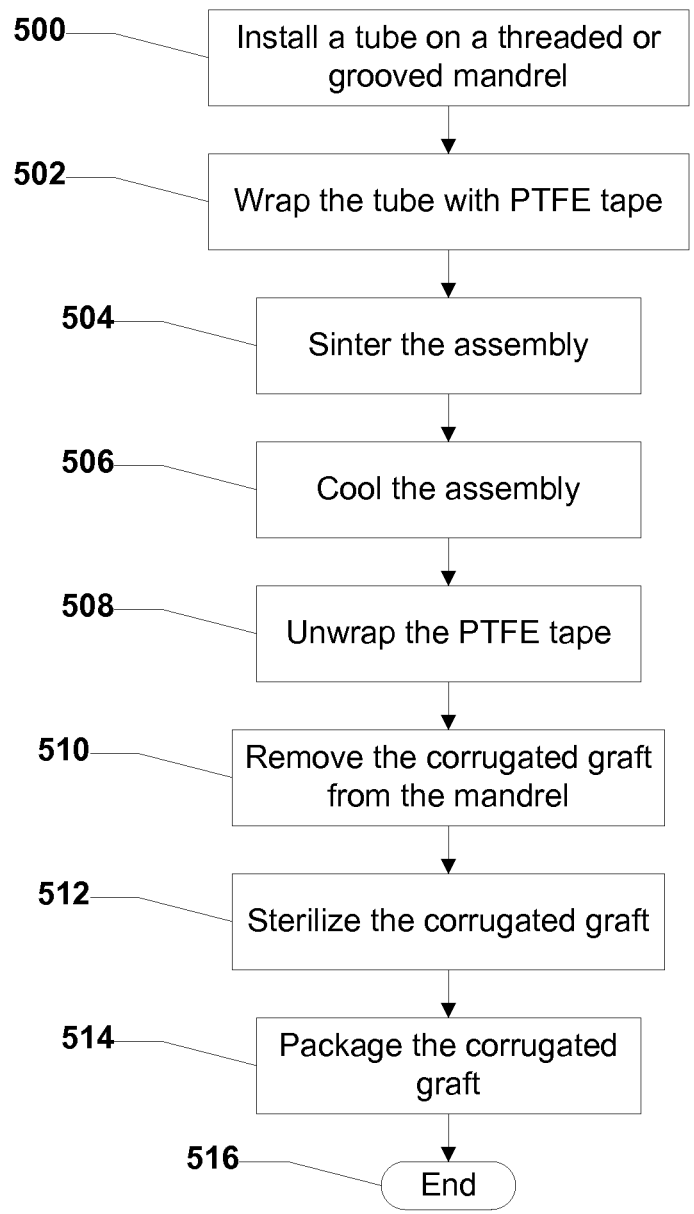
FIG. 5 is a flow chart illustrating an embodiment of a method of making a corrugated graft.

Referring now to FIG. 5, a method of making a corrugated graft is shown and commences at block 500. At block 500, a tube is in installed on a threaded or grooved mandrel. At block 502, the tube can be wrapped with tape, e.g., polytetrafluoroethylene (PTFE) tape. The tape can force the tube into the grooves or threads formed on the mandrel. In another embodiment, a wire, a beading, or similar device can be wound around the tube in order to force the tube into the grooves or threads formed on the mandrel. In yet another embodiment, a mold can be placed around the assembly. The mold can be a two-piece generally block shaped mold formed with a cylindrical bore therein. The cylindrical bore can be formed with internal threads or grooves that can fit into the threads or grooves formed on the mandrel. As such, the mold can further move, or force, the material of the tube into the threads or grooves on the mandrel.

Moving to block 504, the assembly can be sintered, or otherwise heated. In a particular embodiment, the assembly can be sintered, or heated, by placing the assembly in a furnace, or oven, that is initially heated to approximately two hundred and seventy-five degrees Celsius (275° C.). Thereafter, the temperature can be increased to approximately three hundred and twenty-five degrees Celsius (325° C.). In another embodiment, the temperature can be increased to approximately three hundred and thirty degrees Celsius (330° C.). In another embodiment, the temperature can be increased to approximately three hundred and thirty-five degrees Celsius (335° C.). In yet another embodiment, the temperature can be increased to approximately three hundred and forty degrees Celsius (340° C.). In still another embodiment, the temperature can be increased to approximately three hundred and forty-five degrees Celsius (345° C.). In still yet another embodiment, the temperature can be increased to approximately three hundred and fifty degrees Celsius (350° C.). In another embodiment, the temperature can be increased to approximately three hundred and fifty-five degrees Celsius (355° C.). In yet another embodiment, the temperature can be increased to approximately three hundred and sixty degrees Celsius (360° C.). In yet still another embodiment, the temperature can be increased to approximately three hundred and sixty-five degrees Celsius (365° C.). In a particular embodiment, the temperature does not exceed three hundred and sixty-five degrees Celsius (365° C.).

Returning to the description of the method, at block 506, the assembly can be cooled. Further, at block 508, the tape can be unwrapped, or otherwise removed, from the newly formed corrugated graft. If a mold is used, the mold can be removed prior to removal of the tape. At block 510, the corrugated graft can be removed from the mandrel. If the mandrel is threaded, the corrugated graft can be removed from the mandrel by twisting the corrugated graft relative to the mandrel to unthread the corrugated graft from the mandrel. Thereafter, at block 512, the corrugated graft can be sterilized. At block 514, the corrugated graft can be packaged for shipping. The method can then end at state 516. In a particular embodiment, the mandrel can be collapsible in order to facilitate removal of the assembly from the mandrel.

Description of a Method of Making a Corrugated Stent Graft

Figure 6:
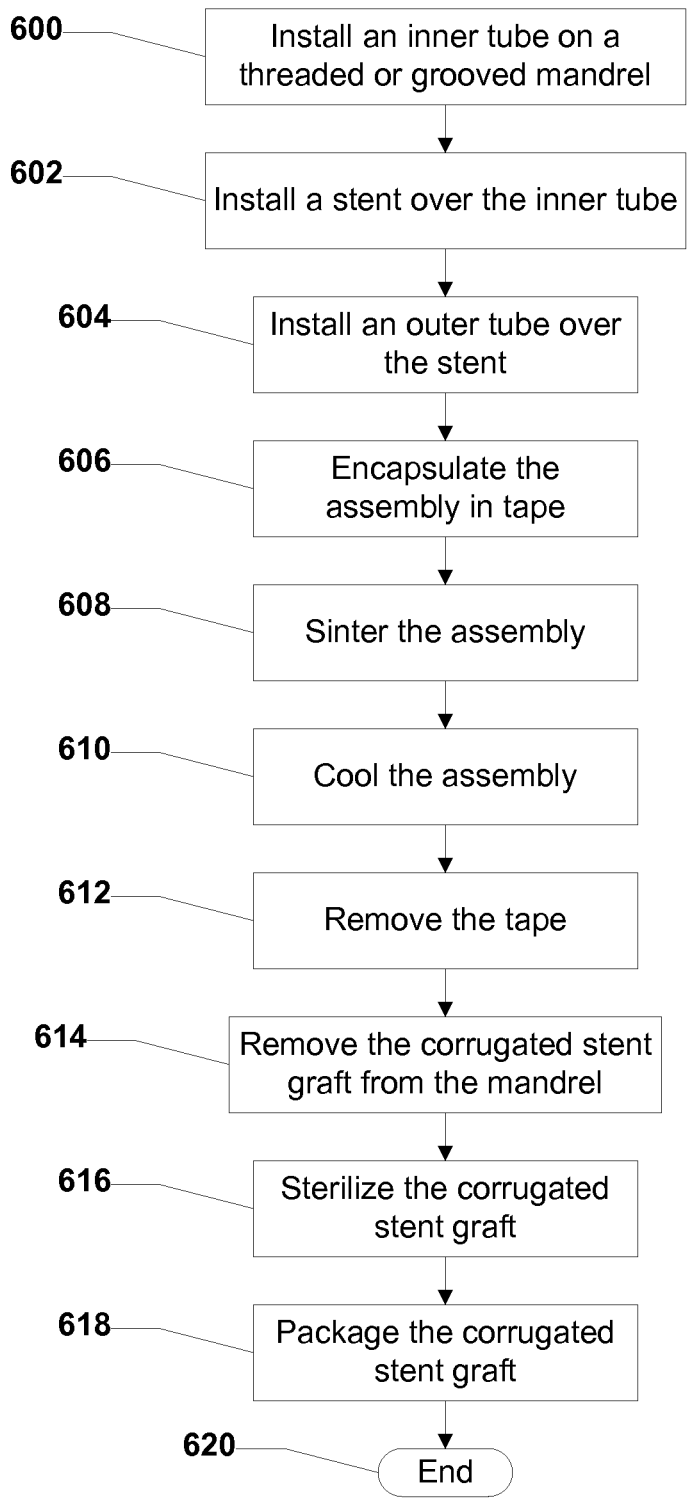
FIG. 6 is a flow chart illustrating a first embodiment of a method of making a corrugated stent graft.

Referring now to FIG. 6, a first embodiment of a method of making a corrugated graft is shown and commences at block 600. At block 600, an inner tube is in installed on a threaded or grooved mandrel. At block 602, a stent can be installed over the inner tube. In a particular embodiment, the stent can be placed over the inner tube so that one or more grooves formed in the mandrel bisect a corresponding group of cells formed in the stent. Thereafter, at block 604, an outer tube can be installed over the stent.

At block 606, the assembly can be wrapped with tape, e.g., polytetrafluoroethylene (PTFE) tape. Moving to block 608, the assembly can be sintered, or otherwise heated. At block 610, the assembly can be cooled. Further, at block 612, the tape can be removed, e.g., unwrapped, from the newly formed corrugated stent graft. If a mold is used, the mold can be removed prior to removal of the tape. At block 614, the corrugated stent graft can be removed from the mandrel. Thereafter, at block 616, the corrugated stent graft can be sterilized. At block 618, the corrugated graft can be packaged for shipping. The method can then end at state 620.

In an alternative embodiment, the inner tube can be formed with corrugations before the stent is installed thereon. Further, the stent can be stretched before it is installed over a corrugated inner tube. For example, the stent can be stretched to increase its length by approximately five percent (5%). Alternatively, the stent can be stretched to increase its length by approximately ten percent (10%). In another embodiment, the stent is stretched to increase its length by approximately fifteen percent (15%). In yet another embodiment, the stent is not stretched more that than twenty percent (20%). After the stent is stretched and placed over the inner tube, an outer corrugated tube can be installed over the stent. Thereafter, the entire assembly can be wrapped and sintered as described herein. After the assembly is cooled, the stent can relax partially or completely to its original length. The corrugations in the tubes can accommodate the relaxation of the stent.

Figure 7:
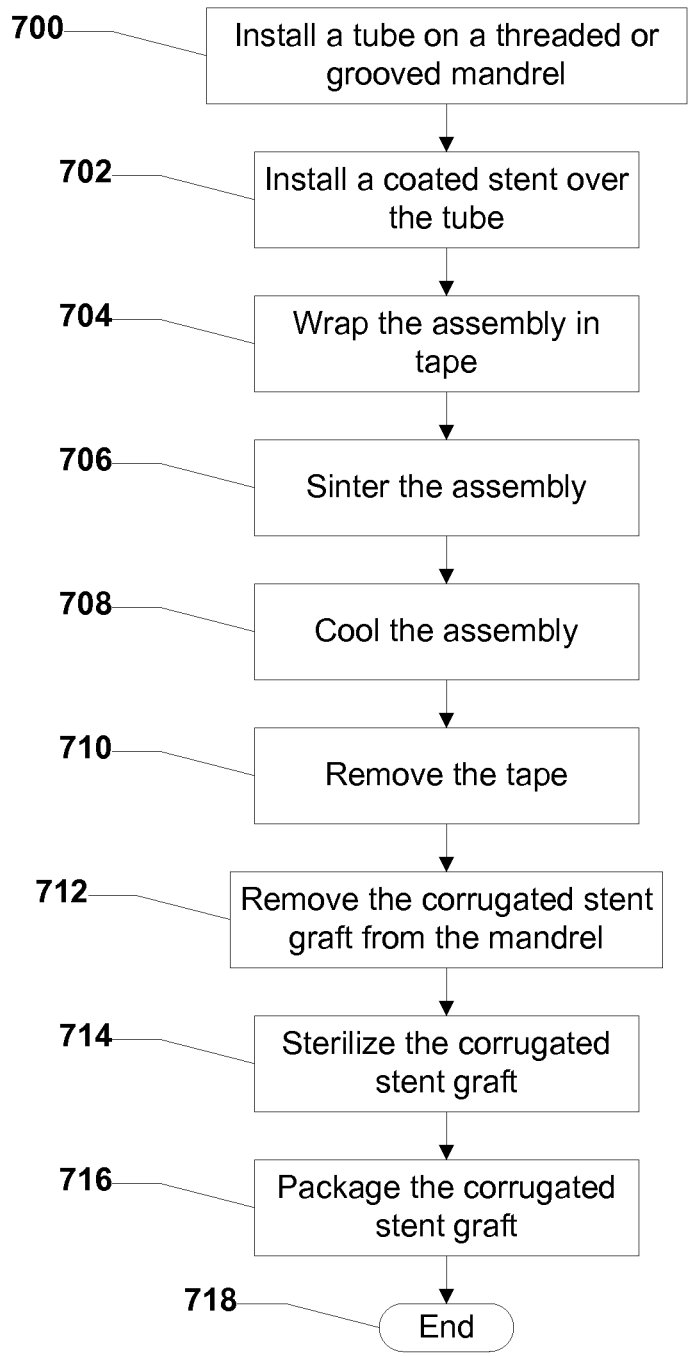
FIG. 7 is a flow chart illustrating a second embodiment of a method of making a corrugated stent graft.

FIG. 7 illustrates a second embodiment of a method of making a corrugated graft. Beginning at block 700, a tube is in installed on a threaded or grooved mandrel. At block 702, a coated stent can be installed over the inner tube. In a particular embodiment, the coated stent can be a nitinol stent coated with a polymer material. In a particular embodiment, the coating has a thickness in a range of five microns to one hundred microns. Further, in a particular embodiment, the polymer material can withstand relatively high temperatures and have a relative low coefficient of friction. For example, the polymer can be a perfluoropolymer.

Moving to block 704, the assembly can be wrapped with tape, e.g., polytetrafluoroethylene (PTFE) tape. At block 706, the assembly can be sintered, or otherwise heated. In a particular embodiment, the assembly can be sintered by placing the assembly in a furnace, or oven, that is heated to approximately three hundred and twenty-five degrees Celsius (325° C.) for approximately ten and one half minutes (10.5 min). In another embodiment, the assembly can be sintered at approximately three hundred and thirty degrees Celsius (330°). In another embodiment, the assembly can be sintered at approximately three hundred and thirty-five degrees Celsius (335° C.). In yet another embodiment, the assembly can be sintered at approximately three hundred and forty degrees Celsius (340° C.). In another embodiment, the assembly can be sintered at approximately three hundred and forty-five degrees Celsius (345° C.). In still another embodiment, the assembly can be sintered at approximately three hundred and fifty degrees Celsius (350° C.). In another embodiment, the assembly can be sintered at approximately three hundred and fifty-five degrees Celsius (355° C.). In yet still another embodiment, the assembly can be sintered at approximately three hundred and sixty degrees Celsius (360° C.). In still another embodiment, the assembly can be sintered at approximately three hundred and sixty-five degrees Celsius (365° C.). In a particular embodiment, the sintering temperature does not exceed three hundred and sixty-five degrees Celsius (365° C.).

Then, at block 708, the assembly can be cooled. At block 710, the tape can be removed, e.g., unwrapped, from the newly formed corrugated stent graft. If a mold is used, the mold can be removed prior to removal of the tape. At block 712, the corrugated stent graft can be removed from the mandrel. Thereafter, at block 714, the corrugated stent graft can be sterilized. At block 716, the corrugated stent graft can be packaged for shipping. The method can then end at state 718.

Description of a First Embodiment of a Beaded Stent Graft

Figure 8:
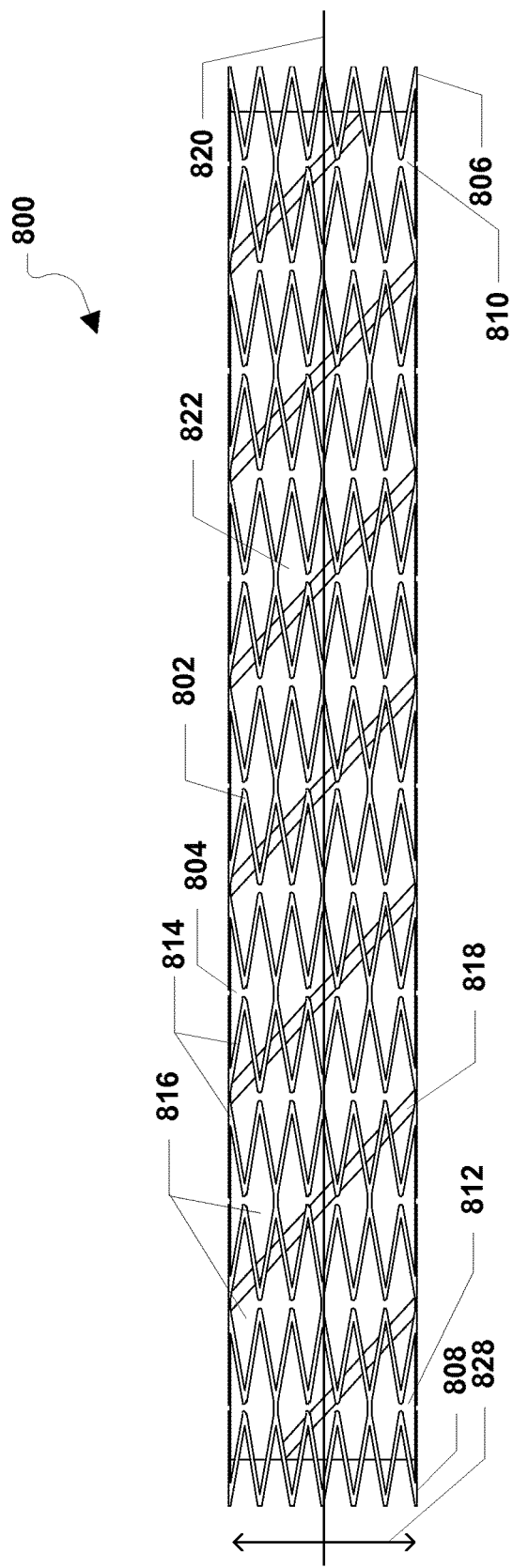
FIG. 8 is a plan view of a first embodiment of a beaded stent graft in a collapsed configuration.
Figure 9:
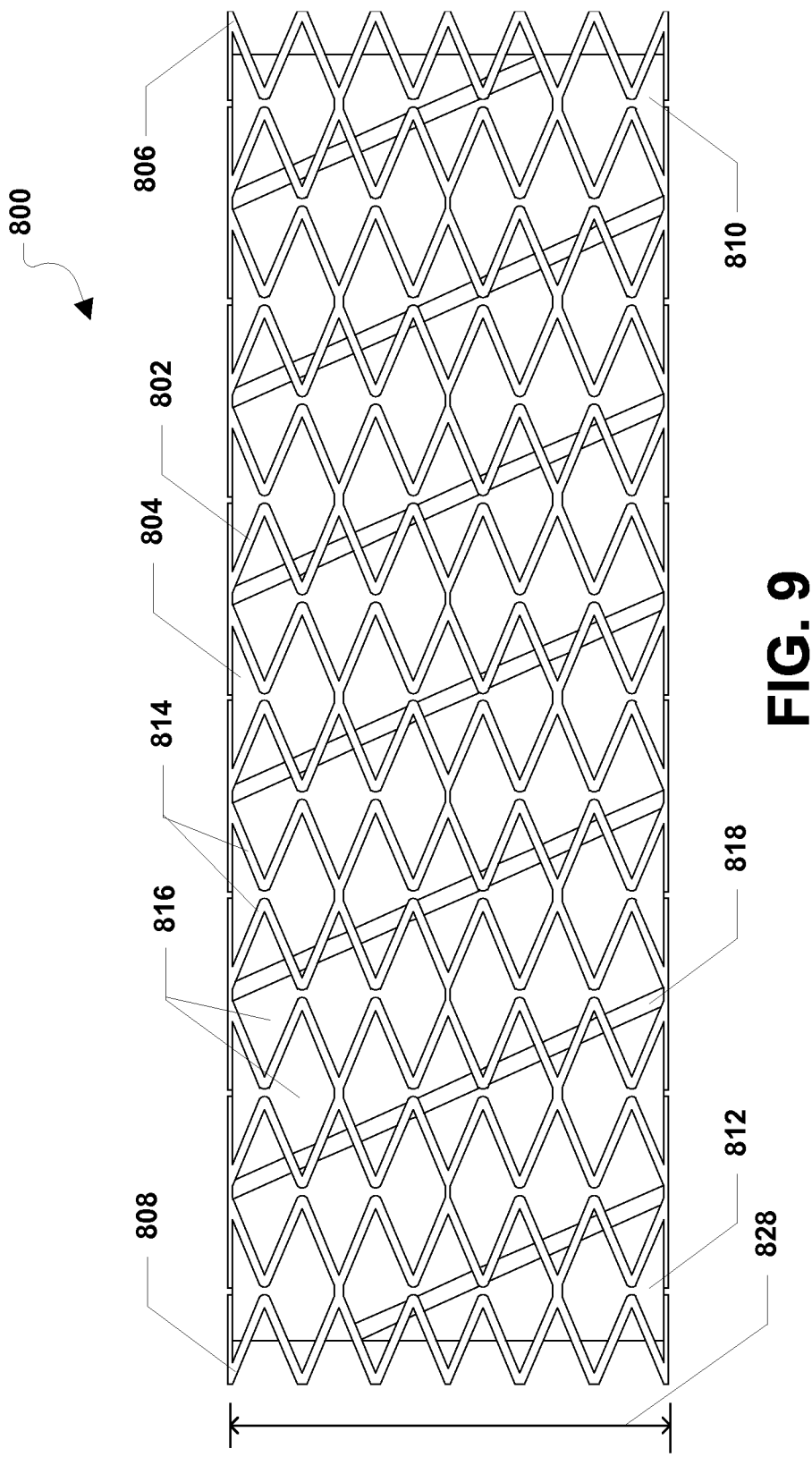
FIG. 9 is a plan view of the first embodiment of the beaded stent graft in an expanded configuration.

Referring to FIG. 8 and FIG. 9, a first embodiment of a beaded stent graft is shown and is generally designated 800. As shown, the beaded stent graft 800 can include a stent 802 and a graft 804. The stent 802 can be hollow and generally cylindrical. Further, the stent 802 can include a proximal end 806 and a distal end 808. The graft 804 can also be hollow and generally cylindrical. Also, the graft 804 can include a proximal end 810 and a distal end 812.

As indicated in FIG. 8 and FIG. 9, the stent 802 can include a plurality of struts 814. Further, the struts 814 can be arranged to establish a plurality of cells 816 within the stent 802. FIG. 8 and FIG. 9 also show that the beaded stent graft 800 can include a plurality of protrusions, e.g., formed by a bead 818 wound around the graft 804. In a particular embodiment, the bead 818 can be a generally flat, fiber, ribbon, tape, or filament. Alternatively, the bead 818 can have a cross-section that is round, elliptical, square, rectangular, semi-circular, or a combination thereof.

In a particular embodiment, the bead 818 can be generally helically shaped. In a particular embodiment, the bead 818 can improve the flexibility of the beaded stent graft 800 and substantially minimize the likelihood of the beaded stent graft 800 kinking when it is bent, e.g., after the beaded stent graft 800 is installed within a patient.

In a particular embodiment, the beaded stent graft 800 can include a predetermined number of windings per inch (in) length of the beaded stent graft 800. For example, the beaded stent graft 800 can include at least ten windings per inch (10/in). In another embodiment, the beaded stent graft 800 can include at least twenty windings per inch (20/in). In yet another embodiment, the beaded stent graft 800 can include at least thirty windings per inch (30/in). In another embodiment, the beaded stent graft 800 can include at least forty windings per inch (40/in). In another embodiment, the beaded stent graft 800 can include at least fifty windings per inch (50/in). In another embodiment, the beaded stent graft 800 can include at least sixty windings per inch (60/in). In another embodiment, the beaded stent graft 800 can include at least seventy windings per inch (70/in). In another embodiment, the beaded stent graft 800 can include at least eighty windings per inch (80/in). In another embodiment, the beaded stent graft 800 can include at least ninety windings per inch (90/in). In another embodiment, the beaded stent graft 800 can include at least one hundred windings per inch (100/in).

As shown in FIG. 8 and FIG. 9, the bead 818 is wound at an angle with respect to a longitudinal axis 820. As such, the bead 818 can form a bead angle 822 with respect to the longitudinal axis 820. In a particular embodiment, the bead angle 822 can be at least five degrees (5°). In another embodiment, the bead angle 822 can be at least ten degrees (10°). In yet another embodiment, the bead angle 822 can be at least fifteen degrees (15°). In still another embodiment, the bead angle 822 can be at least twenty degrees (20°). In another embodiment, the bead angle 822 can be at least twenty-five degrees (25°). In still yet another embodiment, the bead angle 822 can be at least thirty degrees (30°). In yet still another embodiment, the bead angle 822 can be at least thirty-five degrees (35°). In another embodiment, the bead angle 822 can be at least forty degrees (40°). In yet another embodiment, the bead angle 822 is no greater than forty-five degrees (45°).

Figure 10:
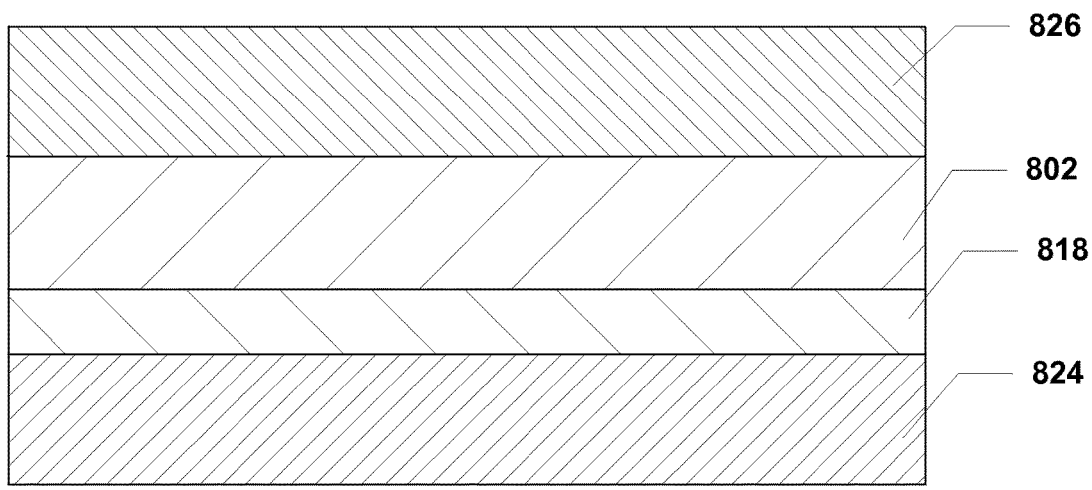
FIG. 10 is a cross-section view of a portion of the first beaded stent graft.

As shown in FIG. 10, which is a cross-section of the beaded stent graft 800 taken through a strut, the stent 802 can be sandwiched, or otherwise formed, between a first graft layer 824 and a second graft layer 826. Further, the bead 818 can be wound around the first graft layer 824. The stent 802 and graft 804 can form an integral structure and as the stent 802 expands, as described below, the graft 804 can expand therewith. Further, as the stent 802 is bent, the graft 804 can bend therewith.

In a particular embodiment the beaded stent graft 800 can be formed without the stent 802. In such a case, the beaded stent graft 800 can be considered a beaded graft. Further, such a corrugated graft can be formed using one of the methods described herein by omitting the stent 802 from the assembled structure.

In another particular embodiment, the beaded stent graft 800 can be movable between a collapsed configuration, shown in FIG. 8, and an expanded configuration, shown in FIG. 9. FIG. 8 and FIG. 9 show that the beaded stent graft 800 can have a diameter 828. The diameter 828 of the beaded stent graft 800, in the collapsed configuration, is relatively smaller than the diameter 828 of the beaded stent graft 800 in the expanded configuration. In the collapsed configuration, the cells 816 within the stent 802 can be collapsed, or otherwise compressed, as indicated in FIG. 8. Conversely, in the expanded configuration the cells 816 within the stent body 802 can be expanded, as indicated in FIG. 9.

Further, the beaded stent graft 800 can have a relatively low kink radius. In other words, the beaded stent graft 800 can be bent around a particular radius without kinking. For example, the beaded stent graft 800 can have a kink radius less than or equal to twenty millimeters (20 mm). In another embodiment, the beaded stent graft 800 can have a kink radius less than or equal to fifteen millimeters (15 mm). In another embodiment, the beaded stent graft 800 can have a kink radius less than or equal to ten millimeters (10 mm). In another embodiment, the beaded stent graft 800 can have a kink radius less than or equal to five millimeters (5 mm). In another embodiment, the beaded stent graft 800 can have a kink radius that is not less than three millimeters (3 mm).

In a particular embodiment, the stent 802 of the beaded stent graft 800 can be made from a shape memory material. The shape memory material can include a shape memory polymer, a shape memory metal, or a combination thereof. Further, the shape memory metal can include a metal alloy. The metal alloy can be a nickel titanium alloy, e.g., nitinol. Further, the graft 804 of the beaded stent graft 800 can be made from a polymer material. In a particular embodiment, the polymer material can be a fluoropolymer material. Moreover, the fluoropolymer material can be an expanded polytetrafluoroethylene (ePTFE). In a particular embodiment, the beaded stent graft 800 can be formed using the method described in conjunction with FIG. 11.

The graft 804 can be formed using an extrusion process. For example, the ePTFE can be mixed with a lubricant, extruded, expanded, and then, sintered. Alternatively, the graft 804 can be made using a wrapping method. The internodal distance for the ePTFE can be in a range of ten to one hundred microns. Alternatively, the internodal distance can be in a range of ten to forty microns.

Description of a Method of Making a Beaded Stent Graft

Figure 11:
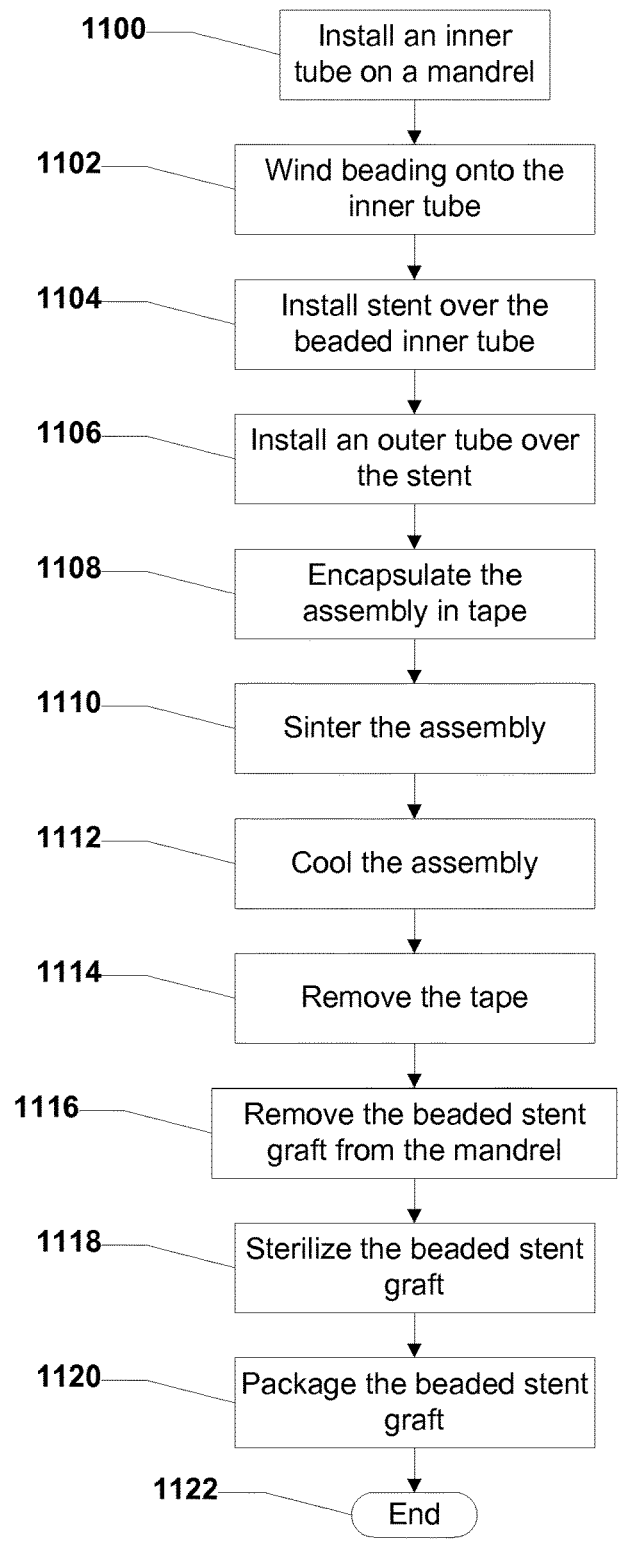
FIG. 11 is a flow chart illustrating a first embodiment of a method of making a beaded stent graft.

Referring now to FIG. 11, a first embodiment of a method of making a corrugated graft is shown and commences at block 1100. At block 1100, an inner tube is in installed on a mandrel, e.g., a smooth mandrel. In a particular embodiment, the inner tube has a thickness in a range of one hundred microns to one hundred and twenty-five microns. At block 1102, a bead can be wound onto the inner tube. In a particular embodiment, the bead has a thickness in a range of ten microns to thirty microns. Further, the bead is substantially flat. The bead can be made from a metal, a polymer, a ceramic, or a combination thereof. The polymer can include PTFE, ePTFE, polyurethane, polyethylene, polypropylene, polyimide, polysulfone, or a combination thereof. Additionally, the polymer can include a filler material adjust the mechanical properties of the beading, e.g., to make the beading stiffer. The filler material can include silica, titanium dioxide, barium sulfate, hydroxyapatite, calcium carbonate, or a combination thereof. Other agents, e.g., a radiopaque agent, an MRI contrast agent, etc., can be added to the bead. Moreover, a bioactive compound can be added to the bead. For example, the bioactive compound can include an anti-restenosis compound. The anti-restenosis compound can include paclitaxel, rapamycin, or a combination thereof.

Moreover, at block 1104, a stent can be installed over the inner tube and the bead. Thereafter, at block 1106, an outer tube can be installed over the stent. The outer tube can have a thickness in a range of one hundred microns to one hundred and twenty-five microns.

At block 1108, the assembly can be wrapped with tape, e.g., polytetrafluoroethylene (PTFE) tape. Moving to block 1110, the assembly can be sintered, or otherwise heated. At block 1112, the assembly can be cooled. Further, at block 1114, the tape can be removed, e.g., unwrapped, from the newly formed beaded stent graft. At block 1116, the beaded stent graft can be removed from the mandrel. Thereafter, at block 1118, the beaded stent graft can be sterilized. At block 1120, the beaded stent graft can be packaged for shipping. The method can then end at state 1122.

Description of a Second Embodiment of a Beaded Stent Graft

Figure 12:
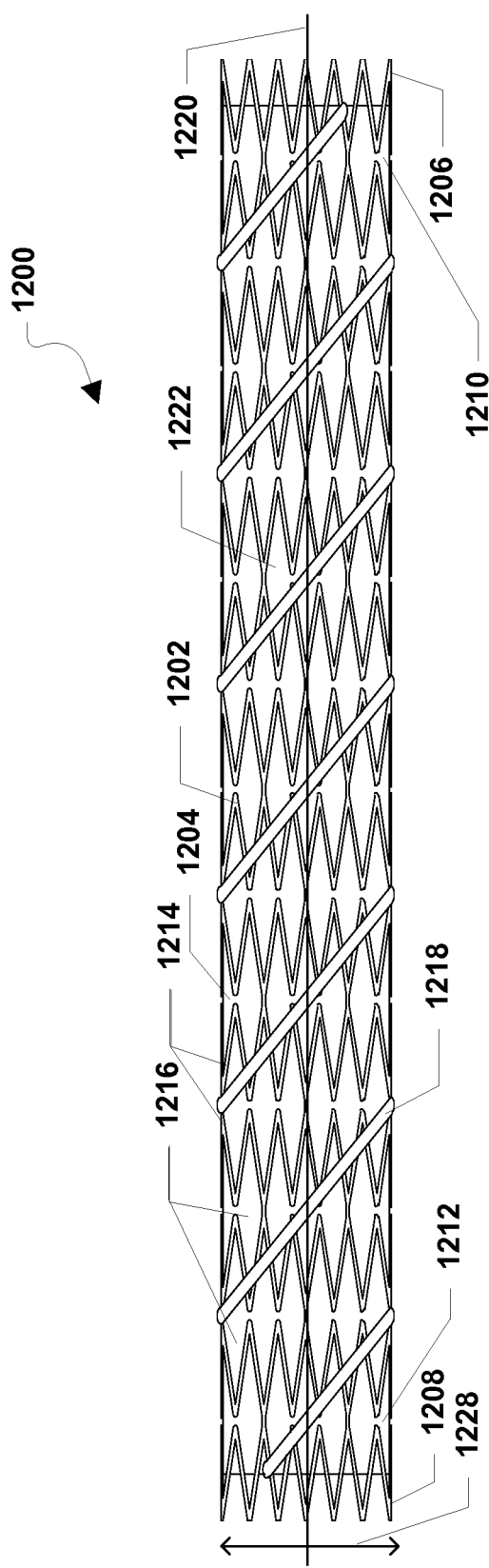
FIG. 12 is a plan view of a second embodiment of a beaded stent graft in a collapsed configuration.
Figure 13:
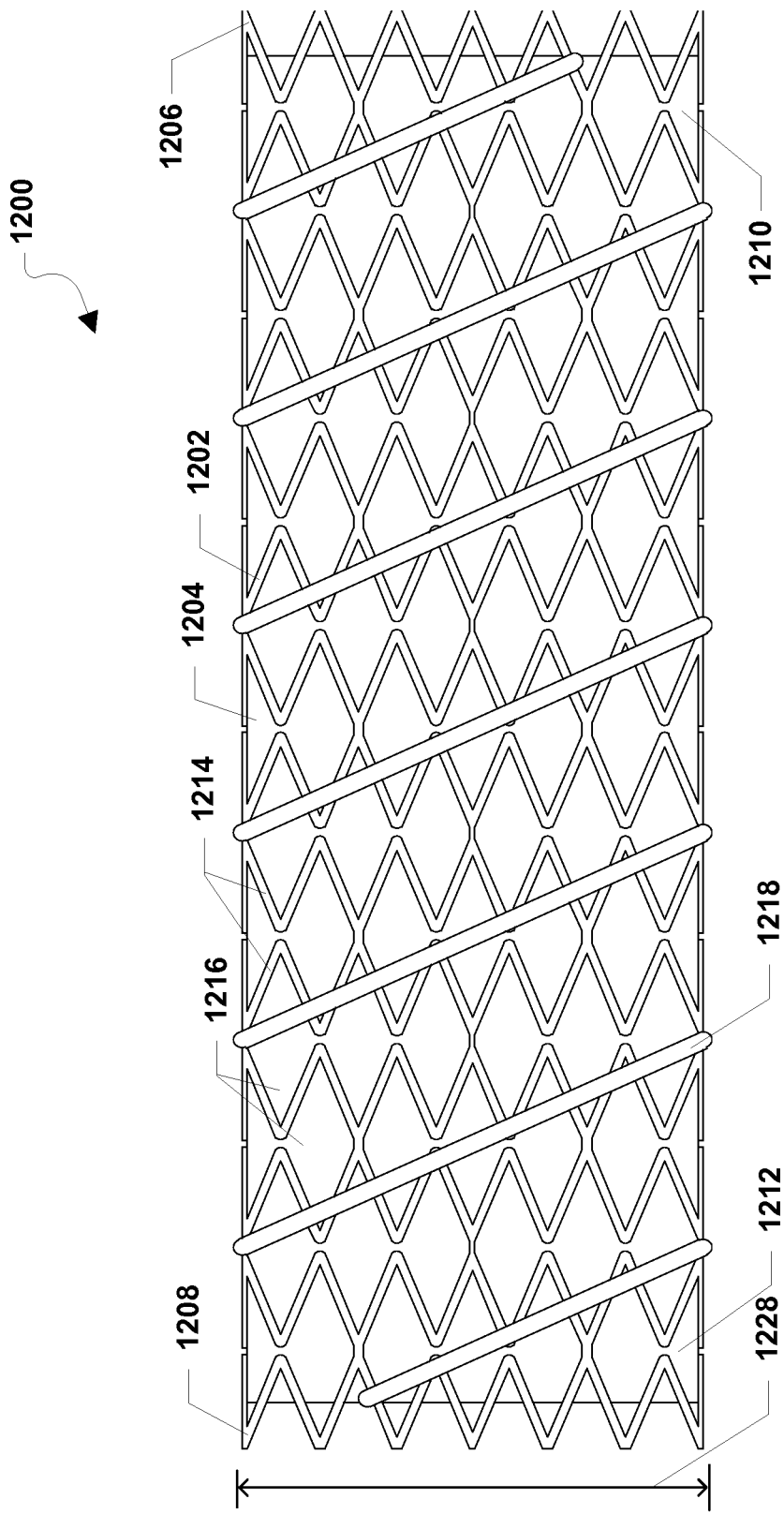
FIG. 13 is a plan view of the second embodiment of the beaded stent graft in an expanded configuration.

Referring to FIG. 12 and FIG. 13, a second embodiment of a beaded stent graft is shown and is generally designated 1200. As shown, the beaded stent graft 1200 can include a stent 1202 and a graft 1204. The stent 1202 can be hollow and generally cylindrical. Further, the stent 1202 can include a proximal end 1206 and a distal end 1208. The graft 1204 can also be hollow and generally cylindrical. Also, the graft 1204 can include a proximal end 1210 and a distal end 1212.

As indicated in FIG. 12 and FIG. 13, the stent 1202 can include a plurality of struts 1214. Further, the struts 1214 can be arranged to establish a plurality of cells 1216 within the stent 1202. FIG. 12 and FIG. 13 also show that the beaded stent graft 1200 can include a bead 1218 wound around the graft 1204. In a particular embodiment, the bead 1218 can be generally helically shaped. In a particular embodiment, the bead 1218 can improve the flexibility of the beaded stent graft 1200 and substantially minimize the likelihood of the beaded stent graft 1200 kinking when it is bent, e.g., after the beaded stent graft 1200 is installed within a patient.

In a particular embodiment, the beaded stent graft 1200 can include a predetermined number of windings per inch (in) length of the beaded stent graft 1200. For example, the beaded stent graft 1200 can include at least ten winding per inch (10/in). In another embodiment, the beaded stent graft 1200 can include at least twenty windings per inch (20/in). In yet another embodiment, the beaded stent graft 1200 can include at least thirty windings per inch (30/in). In another embodiment, the beaded stent graft 1200 can include at least forty windings per inch (40/in). In another embodiment, the beaded stent graft 1200 can include at least fifty windings per inch (50/in). In another embodiment, the beaded stent graft 1200 can include at least sixty windings per inch (60/in). In another embodiment, the beaded stent graft 1200 can include at least seventy windings per inch (70/in). In another embodiment, the beaded stent graft 1200 can include at least eighty windings per inch (80/in). In another embodiment, the beaded stent graft 1200 can include at least ninety windings per inch (90/in). In another embodiment, the beaded stent graft 1200 can include at least one hundred windings per inch (100/in).

As shown in FIG. 12 and FIG. 13, the bead 1218 is wound at an angle with respect to a longitudinal axis 1220. As such, the bead 1218 can form a bead angle 1222 with respect to the longitudinal axis 1220. In a particular embodiment, the bead angle 1222 can be at least five degrees (5°). In another embodiment, the bead angle 1222 can be at least ten degrees (10°). In yet another embodiment, the bead angle 1222 can be at least fifteen degrees (15°). In still another embodiment, the bead angle 1222 can be at least twenty degrees (20°). In another embodiment, the bead angle 1222 can be at least twenty-five degrees (25°). In still yet another embodiment, the bead angle 1222 can be at least thirty degrees (30°). In yet still another embodiment, the bead angle 1222 can be at least thirty-five degrees (35°). In another embodiment, the bead angle 1222 can be at least forty degrees (40°). In yet another embodiment, the bead angle 1222 can be at least forty-five degrees (45°).

Figure 14:
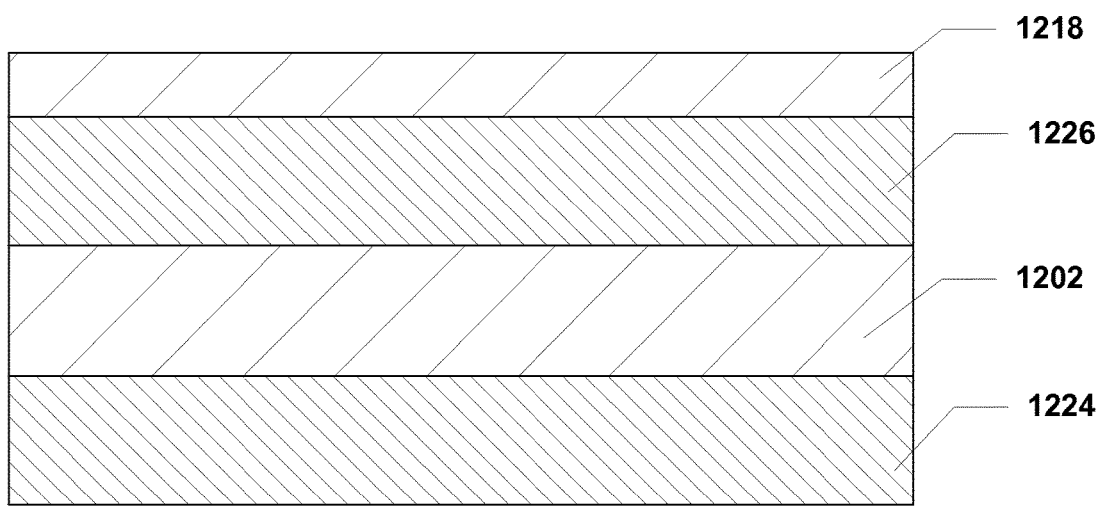
FIG. 14 is a cross-section view of a portion of the second corrugated stent graft.

As shown in FIG. 14, which is a cross-section taken through the beaded stent graft 1200 at a strut, the stent 1202 can be sandwiched, or otherwise formed, between a first graft layer 1224 and a second graft layer 1226. Further, the bead 1218 can be wound around the second graft layer 1226. The stent 1202 and graft 1204 can form an integral structure and as the stent 1202 expands, as described below, the graft 1204 can expand therewith. Further, as the stent 1202 is bent, the graft 1204 can bend therewith.

In another particular embodiment, the beaded stent graft 1200 can be movable between a collapsed configuration, shown in FIG. 12, and an expanded configuration, shown in FIG. 13. FIG. 12 and FIG. 13 show that the beaded stent graft 1200 can have a diameter 1228. The diameter 1228 of the beaded stent graft 1200, in the collapsed configuration, is relatively smaller than the diameter 1228 of the beaded stent graft 1200 in the expanded configuration. In the collapsed configuration, the cells 1216 within the stent 1202 can be collapsed, or otherwise compressed, as indicated in FIG. 12. Conversely, in the expanded configuration the cells 1216 within the stent body 1202 can be expanded, as indicated in FIG. 13.

Further, the beaded stent graft 1200 can have a relatively low kink radius. In other words, the beaded stent graft 1200 can be bent around a particular radius without kinking. For example, the beaded stent graft 1200 can have a kink radius less than or equal to twenty millimeters (20 mm). In another embodiment, the beaded stent graft 1200 can have a kink radius less than or equal to fifteen millimeters (15 mm). In another embodiment, the beaded stent graft 1200 can have a kink radius less than or equal to ten millimeters (10 mm). In another embodiment, the beaded stent graft 1200 can have a kink radius less than or equal to five millimeters (5 mm). In another embodiment, the beaded stent graft 1200 can have a kink radius that is not less than three millimeters (3 mm).

In a particular embodiment, the stent 1202 of the beaded stent graft 1200 can be made from a shape memory material. The shape memory material can include a shape memory polymer, a shape memory metal, or a combination thereof. Further, the shape memory metal can include a metal alloy. The metal alloy can be a nickel titanium alloy, e.g., nitinol. Further, the graft 1204 of the beaded stent graft 1200 can be made from a polymer material. In a particular embodiment, the polymer material can be a fluoropolymer material. Moreover, the fluoropolymer material can be an expanded polytetrafluoroethylene (ePTFE). In a particular embodiment, the beaded stent graft 1200 can be formed using the method described in conjunction with FIG. 15.

Description of a Method of Making a Beaded Stent

Figure 15:
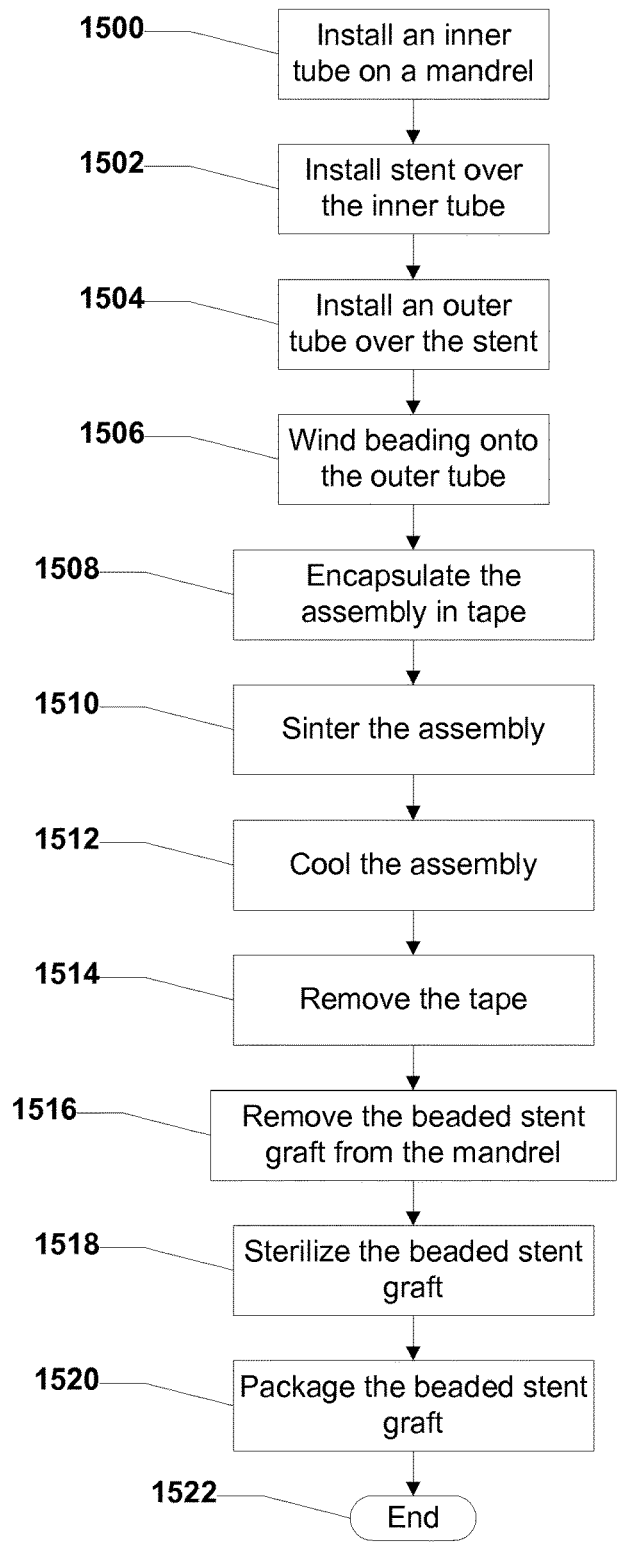
FIG. 15 is a flow chart illustrating a second embodiment of a method of making a beaded stent graft.

Referring now to FIG. 15, a second embodiment of a method of making a corrugated graft is shown and commences at block 1500. At block 1500, an inner tube is in installed on a mandrel, e.g., a smooth mandrel. At block 1502, a stent can be installed over the inner tube. Further, at block 1504, an outer tube can be installed over the stent. At block 1506, a bead can be wound onto, or around, the outer tube.

At block 1508, the assembly can be wrapped with tape, e.g., polytetrafluoroethylene (PTFE) tape. Moving to block 1510, the assembly can be sintered, or otherwise heated. At block 1512, the assembly can be cooled. Further, at block 1514, the tape can be removed, e.g., unwrapped, from the newly formed beaded stent graft. At block 1516, the beaded stent graft can be removed from the mandrel. Thereafter, at block 1518, the beaded stent graft can be sterilized. At block 1520, the beaded stent graft can be packaged for shipping. The method can then end at state 1522.

Conclusion

Embodiments described herein provide a stent graft that can be installed or deployed in locations, which require a robust design. For example, the stent graft can be installed within a joint, such as a knee or elbow, which is subject to repeated bending. When installed in such a location, embodiments described herein are configured to minimize kinking of the stent graft. As such, blood flow through the stent graft will not be restricted or cut-off due to kinking of the stent graft.

One or more embodiments herein can include a bead wound around a stent, e.g., a layer disposed on a stent. Alternatively, the bead can be wound around an inner layer and the stent can be disposed over the bead and the inner layer. In yet another embodiment, the bead can be woven through the stent, e.g., woven through the struts of the stent as the bead is helically wound around the stent. Thereafter, the stent can be encapsulated between one or more layers, as described herein. Further, as described herein, one or more embodiments can include an inner layer and an outer layer with a stent sandwiched there between. Alternative embodiments may only include an outer layer or an inner layer. For example, a stent can be placed on an outer layer and thereafter, a bead may be wound directly on the stent.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A stent graft, comprising:
   a stent, including a plurality of struts arranged to establish a plurality of rings along a longitudinal axis of the stent graft, wherein adjacent rings are directly connected; and
   a graft engaged with the stent, wherein:
      the graft includes an inner graft layer and an outer graft layer,
      at least one of the inner graft layer and the outer graft layer includes a plurality of protrusions as viewed in cross section extending through the longitudinal axis,
      the plurality of protrusions form a plurality of closed loops, the directly connected adjacent rings bisected by at least one closed loop,
      the plurality of protrusions are formed by at least one bead wound around the inner graft layer, the outer graft layer, or a combination thereof; and
      the at least one bead is sintered to the inner graft layer, the outer graft layer, or a combination thereof.

* * * * *